United States Patent [19]

Slifkin

[11] Patent Number: 5,250,410
[45] Date of Patent: Oct. 5, 1993

[54] RAPID DETECTION OF HERPES VIRUS WITH LECTIN

[75] Inventor: Malcolm Slifkin, Pittsburgh, Pa.

[73] Assignee: Allegheny-Singer Research Institute, Pittsburgh, Pa.

[21] Appl. No.: 947,962

[22] Filed: Sep. 21, 1992

Related U.S. Application Data

[63] Continuation of Ser. No. 810,460, Dec. 18, 1991, abandoned, which is a continuation of Ser. No. 7,137, Jan. 27, 1987, abandoned.

[51] Int. Cl.$^5$ .................. C12Q 1/70; G01N 33/00
[52] U.S. Cl. .................................. 435/5; 435/7.1;
  435/7.2; 435/7.21; 435/29; 435/34;
  435/240.206; 436/501; 436/811; 436/827;
  530/396
[58] Field of Search .................. 435/4.5, 7.1, 7.2, 7.21,
  435/29, 34, 240.21, 237, 235.1, 968; 436/501,
  800, 811, 827; 530/395, 396

[56] References Cited

U.S. PATENT DOCUMENTS

| | | | |
|---|---|---|---|
| 4,130,395 | 12/1978 | Chryssanthou | 23/230 B |
| 4,294,817 | 10/1981 | Burgett et al. | 424/8 |
| 4,430,437 | 2/1984 | Hampar et al. | 436/548 |
| 4,745,182 | 5/1988 | Cohen et al. | 436/501 |

OTHER PUBLICATIONS

Nicolson, G., Int Rev. Cytol 39: 89–190 (1974).
Doyle, R., et al., Eur. Journ. Clin. Microbiol, 3(1): 4–9 (1984).
Marquez, E., Chem Abstr. 85 (1976) Abstr No. 157475m.
Svennerholm, B. et al., "Herpes Simplex Virus Type-Selective Enzyme-Linked Immunosorbent Assay with *Helix pomatia* Lectin-Purified Antigens," Journal of Clinical Microbiology, 19(2), 1984, pp. 235–239.
Olofsson, S. et al., "Different Populations of Herpes Simplex Virus Glycoprotein C Discriminated by the Carbohydrate-binding Characteristics of N-acetylgalactosamine Specific Lectins (Soybean and *Helix pomatia*)," Archives of Virology, 86, 1985, pp. 121–128.
Olofsson, S. "Populations of Herpes Simplex Virus Glycoprotein gC with and without Affinity for the N-Acetyl-Galactosamine Specific Lectin of *Helix pomatia*," Archives of Virology, 76, 1983, pp. 25–38.
Mansbridge, Jonathan N. et al., "The Binding of *Helix pomatia* and *Ulex europeus* Agglutinins to Normal and Psoriatic Skin," The Journal of Investigative Dermatology, 82 (2) 1984, pp. 170–175.
Yoshizo Asano, MD, et al., "Five-Year Follow-up Study of Recipients of Live Varicella Vaccine Using Enhanced Neutralization and Fluorescent Antibody Membrane Antigen Assay," Pediactrics, 72(3), 1983, pp. 291–294.
Nerurkar, Lata S. et al., "Detection of Genital Herpes Simplex Infections by a Tissue Culture-Fluorescent-Antibody Technique with Biotin-Avidin," Journal of Clinical Microbiology, 17(1), 1983, pp. 149–154.
Chapel, T. et al., "Influence of genital herpes on results of fluorescent treponemal antibody absorption test," British Journal of Venereal Diseases, 54, 1978, pp. 299–302.

(List continued on next page.)

Primary Examiner—Esther L. Kepplinger
Assistant Examiner—Carol A. Spiegel
Attorney, Agent, or Firm—Webb, Burden, Ziesenheim & Webb

[57] ABSTRACT

A method for the rapid identification and differentiation of HSV-1 and/or HSV-2 with fluorescein-conjugated *Helix pomatia* lectin. Clinical specimens are processed, with centrifugation, in pre-prepared shell vials of cell culture, with subsequent supplementation and 20 hour incubation (approximately) at 37° C. Coverslips of the shell vials are then fixed, air dried, overlaid with fluorescein-conjugated *Helix pomatia* lectin, washed, dried, mounted and examined under a microscope equipped with an ultraviolet light source. The identification of fluorescence confirms herpes virus infection. Granular fluorescent patterns confirm presence of HSV-2 serotype and diffuse fluorescent patterns confirm presence of HSV-1 serotype.

9 Claims, No Drawings

OTHER PUBLICATIONS

Rajcani, J. et al., "Screening of Antibodies to Herpes Simplex Virus in Human Sera by Indirect Immunofluorescence," Acta virol., 17, 1973, pp. 61–68.

Johnson, Lorna D. et al., "Comparison of Indirect Hemagglutination and Indirect Immunogluorescence Tests with Microneutralization Tests for Detection of Type-Specific *Herpesvirus hominis* Antibody," Journal of Clinical Microbiology, 9(3), 1979, pp. 384–390.

Gardner, P. S. et al., "Rapid Diagnosis of *Herpesvirus hominis* Infections in Superficial Lesions by Immunofluorescent Antibody Techniques," British Medical Journal, 4, 1968, pp. 89–92.

Hitchcock, G. et al., "Herpes Simplex Lesions of the Skin Diagnosed by the Immunofluorescence Technique," The Medical Journal of Australia, 2, 1974, pp. 280–284.

Tomlinson, A. H. et al., "Immunofluorescence staining for the diagnosis of herpes encephalitis," J. Clin. Path., 27, 1974, pp. 495–499.

Olofsson, Sigvard et al., "Glycoprotein C of Herpes Simplex Virus Type 1: Characterization of O-linked Oligosaccharides," J. Gen. Virol., 64, 1983, pp. 2735–2747.

Warford, A. L. et al., "Herpes simplex virus testing of an obstetric population with an antigen enzyme-linked immunosorbent assay," Am. J. Obstet. Gynecol., 154(1), 1986, pp. 21–28.

Lee, Francis K. et al., "Detection of Herpes Simplex Virus Type 2-Specific Antibody with Glycoprotein G," Journal of Clinical Microbiology, 22(4), 1985, pp. 641–644.

RAPID DETECTION OF HERPES VIRUS WITH LECTIN

This is a continuation of copending application Ser. No. 07/810,460 filed on Dec. 18, 1991, now abandoned, which was a continuation of the then copending application Ser. No. 07/007,137 filed on Jan. 27, 1987, now abandoned.

FIELD OF THE INVENTION

The present invention relates to the rapid detection and differentiation of herpes simplex virus (HSV-1, HSV-2) with a specific fluorescein-conjugated lectin by a novel, rapid technique.

BACKGROUND OF THE INVENTION

The assay of Herpes Simplex Virus Type 1 (HSV-1) and Type 2 (HSV-2) with *Helix pomatia* lectin has been documented by Svennerholm, B. et al., "Herpes Simplex Virus Type-Selective Enzyme-Linked Immunosorbent Assay with *Helix pomatia* Lectin-Purified Antigens," in *Journal of Clinical Microbiology*, 19(2), 1984, pp. 235–239; Olofsson, S. et al., "Different Populations of Herpes Simplex Virus Glycoprotein C Discriminated by the Carbohydrate-binding Characteristics of N-acetylgalactosamine Specific Lectins (Soybean and *Helix pomatia*)," in *Archives of Virology*, 86, 1985, pp. 121–128, and Olofsson, S., "Populations of Herpes Simplex Virus Glycoprotein gC with and without Affinity for the N-Acetyl-Galactosamine Specific Lectin of *Helix pomatia*," in *Archives of Virology*, 76, 1983, pp. 25–38. Each of these three articles documents the specificity of *Helix pomatia* lectin for HSV-1 and its consequent suitability for use in laboratory assay. For example, Svennerholm et al. conclude that HSV type-specific immunoglobulin G antibodies can be measured by enzyme-linked immunosorbent assay with the use of *Helix pomatia* lectin-purified HSV-1 and HSV-2 antigens.

As with any diagnostic technique which incorporates an enzyme-linked immunosorbent assay (ELISA), however, the typical Svennerholm technique involves complex procedures and expensive equipment, both of which contribute to delay. Additionally, prior art techniques have for various reasons typically required an incubation period of several days. Furthermore, none of the articles cited above teaches or suggests that a particular method of using *Helix pomatia* lectin can give faster or more reliable identification of HSV than can those of the prior art. A need remains, therefore, for a simple, inexpensive and rapid diagnostic test to confirm suspected HSV infection. A need further remains for a unique non-immunological reagent that provides means to differentiate between HSV-1 and HSV-2 serotypes in a single monolayer of HSV infected cells.

SUMMARY OF THE INVENTION

In order to meet these needs, the present invention is a method for the rapid identification of HSV-1 and/or HSV-2 with fluorescein-conjugated *Helix pomatia* lectin. Clinical specimens are processed, with centrifugation, in pre-prepared shell vials of cell culture, with subsequent supplementation and 20 hour incubation (approximately) at 37° C. Coverslips of the shell vials are then fixed, air dried, overlaid with fluorescein-conjugated *Helix pomatia* lectin, washed, dried, mounted and examined under a microscope equipped with an ultraviolet light source. The identification of fluorescence confirms herpes simplex virus infection. Furthermore, the differentiation of HSV-1 and HSV-2 is also provided with the respective fluorescent patterns of the infected cells labeled with the fluorescein-bound lectin reagent.

DETAILED DESCRIPTION OF THE INVENTION

Lectins are specific carbohydrate-binding proteins of non-immune origin. Lectins are therefore generally useful in the immunodiagnostic binding of carbohydrate-containing antigens. Specific lectins accordingly bind antigens having specific carbohydrate segments therein. For example, *Helix pomatia* lectin is specific for N-acetylgalactosamine, and has thus been found to bind a particular class of antigens (glycoproteins gC) which are induced by HSV-1 and HSV-2 and which contain a particular corresponding oligosaccharide.

The present described technique is a method which adapts the above-described binding of HSV antigens with *Helix pomatia* lectin to provide a simple, inexpensive and rapid diagnostic test. The method requires only readily available materials, a minimum of process steps, and basic laboratory equipment. The lectin/antigen binding which occurs when HSV antigen is present is rendered visible by preliminary fluorescein conjugation of the *Helix pomatia* lectin. Reactant aliquot volume and cell culture media are selected to permit antigen identification after an incubation period of only about 20 hours.

A. Clinical Specimens

Clinical specimens are obtained from dermal sites (including oral and/or genital sites) of patients having suspected HSV infections. All specimens, collected on swabs, are received and transported in viral transport medium known in the art. The volume of transport medium is between 1 and 5 ml per swab. If the swabs cannot be processed immediately as described below, they may be held at −20° C. for a maximum of 18 hours before processing. Before use, transport vials containing specimens are mixed on a vortex apparatus (or by manual agitation) for approximately 30 seconds, after which the swab if present is removed after expressing excess liquid onto the inner side of the transport tube.

B. Processing of Clinical Specimens

Cell culture monolayers on coverslips in shell vials are inoculated with an aliquot of the specimen-containing transport medium. For example, the medium from shell vial cultures of cell monolayers is aspirated and replaced with an aliquot of transport medium. The vials are then capped and centrifuged, and subsequently an aliquot of Eagle Minimum Essential Medium is added to each vial. The vials are then incubated at about 37° C. for at least 20 hours, but usually approximately 24 hours.

Subsequent to incubation, the coverslips of the vials are washed in (fixed with) acetone and are overlaid with an aliquot of fluorescein-conjugated *Helix pomatia* lectin. After 5 minutes, the coverslips are then washed with washing fluid, air dried, mounted in mounting fluid and examined. Examination is conducted with a microscope equipped with a mercury lamp or other source of ultraviolet light.

Suitable cell culture monolayers are those which generate glycoprotein gC antigen upon inoculation with HSV. Exemplary of such cell culture preparations are MRC-5 (human diploid lung cell line) available, as a monolayer culture on coverslips in shell vials, from Earl-Clay Laboratories, Inc., Novato, Calif.; BHK-21 (Syrian (golden hamster) kidney cell) monolayer shell cultures, from MA Bioproducts, Walkersville, Md., are likewise suitable for use in the present method.

Centrifugation of the inoculated shell vial should proceed to a degree calculated to ensure substantial infection of the cell culture with any HSV present in the specimen. Preferably, vials are centrifuged at 700×g. (times gravitational force) for 40 minutes at 30° C. in a Sorvall Centrifuge (DuPont). Preferred minimum and maximum centrifugation parameters are 500–900×g. for between 30 and 50 minutes.

Ordinarily, 0.2 ml aliquots of transport medium should be added to the evacuated (aspirated) shell vials, although an aliquot between 0.1–0.3 ml may be used if desired. About 0.5–3.0 ml of Eagle Minimum Essential Medium is added subsequently, although this preferred aliquot volume is 1.0 ml. Optimal working dilution of fluorescein-conjugated *Helix pomatia* lectin in phosphate buffered saline is 500 microgram/ml, applied in aliquots of between 20–30 microliter, preferably 25 microliter. Fluorescein-conjugated *Helix pomatia* lectin concentrate is available from Sigma Pharmaceuticals.

The preferred mounting fluid for use in the above-described technique is the glycerol-buffer mounting fluid well known in the art. Acetone is the preferred fixative; FA buffer (Difco, Detroit, Mich.) is an exemplary washing fluid although a number of others are known in the art and suitable for use.

When the mounted coverslips are examined under magnification and ultraviolet light, granular or large diffuse masses of fluorescent foci are observed in HSV infected cells. Observation of diffuse masses of fluorescent foci confirms the presence of the HSV-1 serotype; granular fluorescent foci confirm the presence of HSV-2 serotype. Thus, observation of intracellular fluorescent foci confirms either HSV-1 or HSV-2 infection, specifically, in the area from which the swab was taken.

EXAMPLE I

The medium from nine MRC-5 shell vials was aspirated. To three of the vials was added 0.2 ml each of transport medium containing a swab specimen. A fourth vial received 0.2 ml uninfected transport medium as a control. The remaining 5 vials were also designated as controls and received a 0.2 ml aliquot of one of each of five known viruses (stock strains): HSV-1; HSV-2; cytomegalovirus; varicella-zoster virus (Ellen strain); and adenovirus type 6. The stock strains were obtained from the American Type Culture Collection, Rockville, Md.

The vials were capped and centrifuged at 700×g. for 40 minutes at 30° C. in a Sorvall Centrifuge. After centrifugation, 1.0 ml of Eagle Minimum Essential Medium was added to each vial, and the vials were incubated at 37° C. for 20 hours.

EXAMPLE 2

Coverslips were removed from eight vials prepared and incubated in accordance with Example 1. The coverslips were washed briefly in acetone, after which each vial was evacuated and filled with fresh acetone. After a five minute incubation at room temperature, the acetone was decanted and the coverslips were air dried. A 25 microliter aliquot of 500 microgram/ml fluorescein-conjugated *Helix pomatia* lectin in phosphate buffered saline was overlaid on each coverslip. The coverslips were washed, after 5 minutes, with FA buffer washing fluid; washing proceeded 10 minutes for each coverslip. The coverslips were air dried and mounted in glycerol-buffer mounting fluid.

Examination of the coverslips was carried out under a microscope and with ultraviolet light. Four of the eight coverslips contained granular masses of fluorescent foci which indicated HSV-2 infection. These four coverslips were those from the two specimen inoculated vials and the two vials containing the known HSV-1 and HSV-2 stock strains. The coverslips for the control vial and the three vials containing cytomegalovirus, varicella-zoster virus and adenovirus were all free from fluorescent foci.

EXAMPLE 3

Example 1 was repeated using BHK-21 shell vials in place of the MRC-5 vials and a specimen taken from a different patient. The prepared inoculated vials were then overlaid with fluorescein-conjugated *Helix pomatia* lectin by the procedure described in Example 2. As with the vials of Example 2, the corresponding four coverslips contained diffuse masses of fluorescent foci which indicated HSV-1 infection.

COMPARATIVE EXAMPLE 4

Three sets each of the sixteen vials of Examples 1 and 3 combined were prepared and incubated. Each coverslip in the first set of vials was overlaid with a 25 microliter aliquot of 500 microgram/ml fluorescein-labeled *D. biflorus* lectin in phosphate buffered saline. Each coverslip in the second set was overlaid with a 25 microliter aliquot of 500 microgram/ml fluorescein-labeled *Glycine max* lectin in phosphate buffered saline, and each coverslip in the third set was overlaid with a 25 microliter aliquot of 500 microgram/ml fluorescein-labeled *W. floribunda* lectin in phosphate buffered saline. After completion of the washing, mounting and examination step outlined in Example 2 the coverslips of all the vials were examined for fluorescent foci. No fluorescent foci were identified.

Although the invention has been described above in reliance upon specific materials and method steps, the present invention is to be limited only insofar as is set forth in the accompanying claims.

I claim:

1. A method for identifying herpes virus in an infected area, comprising the steps of:
   a) collecting a specimen from a patient with a swab and transferring at least a portion of said specimen from said swab to a quantity of viral transport medium;
   b) combining an aliquot of said viral transport medium with a cell culture and centrifuging the resultant combination;
   c) supplementing the combination with growth medium and incubating the supplemented combination for at least about 20 hours at about 37° C.;
   d) fixing the incubated cells derived in step c);
   e) contacting said incubated cells with fluorescein-conjugated *Helix pomatia* lectin; and,
   f) examining said incubated cells for fluorescence wherein the presence of fluorescent foci confirms herpes infection and wherein a diffuse mass pattern of fluorescence indicates HSV-1 serotype and a granular pattern of of fluorescence indicates HSV-2 serotype.

2. The method according to claim 1, wherein step b) further comprises the step of:
   b) combining a 1-5 ml aliquot of said viral transport medium with a cell culture monolayer on a coverslip in a vial and centrifuging the vial at about 500-900×g. for about 30-50 minutes.

3. The method according to claim 1 wherein step c) further comprises the step of:
   c) supplementing said vial with about 1.0 ml Eagle Minimum Essential Medium and incubating said vial for at least about 20 hours at about 37° C.

4. The method according to claim 1 wherein the fixing of step d) comprises the step of:
   d) fixing the incubated cells on said coverslip with an acetone wash of at least about 5 minutes duration.

5. The method according to claim 1 wherein the contracting of step e) comprises the step of:
   e) overlaying said incubated cells with between about 20-30 microliter of 500 microgram/ml fluorescein-conjugated *Helix pomatia* lectin in phosphate buffered saline.

6. The method according to claim 1 wherein the examining of step f) comprises the step of:
   f) washing, drying, mounting and examining said incubated cells for fluorescence.

7. The method according to claim 1 wherein the combining of step b) comprises the step of:
   b) combining an aliquot of said viral transport medium with a human embryonic lung cell culture monolayer and centrifuging the resultant combination at about 700×g. for about 40 minutes.

8. The method according to claim 1 wherein the combining of step b) comprises the step of:
   b) combining an aliquot of said viral transport medium with a human diploid lung cell monolayer and centrifuging the resultant combination at about 700×g. for about 40 minutes.

9. The method according to claim 1 wherein the combining of step b) comprises the step of:
   b) combining an aliquot of said viral transport medium with a Syrian golden hamster kidney cell monolayer and centrifuging the resultant combination at about 700×g. for about 40 minutes.

* * * * *

UNITED STATES PATENT AND TRADEMARK OFFICE
CERTIFICATE OF CORRECTION

PATENT NO. : 5,250,410
DATED : October 5, 1993
INVENTOR(S) : Malcolm Slifkin

It is certified that error appears in the above-indentified patent and that said Letters Patent is hereby corrected as shown below:

On title page, item [56] under References Cited, "OTHER PUBLICATIONS" in Johnson, Lorna D. et al. reference on page 2, "Immunogluorescence" should read --Immunofluorescence--.

Claim 1 Line 67 Column 4 "of of" should read --of--.

Claim 5 Line 18 Column 5 "contracting" should read --contacting--.

Signed and Sealed this

Fifth Day of July, 1994

Attest:

BRUCE LEHMAN

Attesting Officer

Commissioner of Patents and Trademarks